(12) United States Patent
Khanlari et al.

(10) Patent No.: US 10,745,345 B2
(45) Date of Patent: Aug. 18, 2020

(54) ANTI-FOULANT FORMULATION FOR COMPRESSORS

(71) Applicant: ECOLAB USA INC., St. Paul, MN (US)

(72) Inventors: Anahita Khanlari, Houston, TX (US); Andrew R. Neilson, Richmond, TX (US)

(73) Assignee: Ecolab USA Inc., St. Paul, MN (US)

( * ) Notice: Subject to any disclaimer, the term of this patent is extended or adjusted under 35 U.S.C. 154(b) by 122 days.

(21) Appl. No.: 15/903,779

(22) Filed: Feb. 23, 2018

(65) Prior Publication Data
US 2018/0244605 A1 Aug. 30, 2018

Related U.S. Application Data

(60) Provisional application No. 62/463,790, filed on Feb. 27, 2017.

(51) Int. Cl.
*C07C 233/20* (2006.01)
*C07C 231/02* (2006.01)
(Continued)

(52) U.S. Cl.
CPC ............ *C07C 233/20* (2013.01); *C07C 15/24* (2013.01); *C07C 31/202* (2013.01);
(Continued)

(58) Field of Classification Search
CPC ..... C07C 233/20; C07C 231/02; C07C 15/24; C07C 31/202; C10G 75/04; C10G 9/16; C07D 211/76; C07D 211/94; C09K 15/18
See application file for complete search history.

(56) References Cited

U.S. PATENT DOCUMENTS 4,660,645 A * 4/1987 Newlove .............. A61K 9/1635
166/279
5,266,186 A   11/1993 Kaplan
(Continued)

FOREIGN PATENT DOCUMENTS

CN  104039835 A * 9/2014 ........... C07D 211/94
EP  0632121 A2  1/1995
(Continued)

OTHER PUBLICATIONS

International Search Report for International Application No. PCT/US2018/019448, dated May 14, 2018, 6 pages.
(Continued)

*Primary Examiner* — Pamela H Weiss
(74) *Attorney, Agent, or Firm* — Kagan Binder, PLLC

(57) ABSTRACT

Disclosed are compositions and methods for preventing or reducing polymer formation and polymer deposition in equipment used in petrochemical processes. An antifoulant composition includes a combination of one or more antioxidants; one or more antipolymerants; one or more dispersants; and one or more solvents. A method of preventing or reducing fouling of process equipment used in an industrial process is also described. The method includes introducing into the process equipment an antifoulant composition, the antifoulant composition comprising a combination of one or more antioxidants; one or more antipolymerants; one or more dispersants; and one or more solvents.

4 Claims, 1 Drawing Sheet

(51) Int. Cl.
  *C07C 15/24* (2006.01)
  *C10G 75/04* (2006.01)
  *C07D 211/76* (2006.01)
  *C07D 211/94* (2006.01)
  *C09K 15/18* (2006.01)
  *C10G 9/16* (2006.01)
  *C07C 31/20* (2006.01)

(52) U.S. Cl.
  CPC .......... *C07C 231/02* (2013.01); *C07D 211/76* (2013.01); *C07D 211/94* (2013.01); *C09K 15/18* (2013.01); *C10G 9/16* (2013.01); *C10G 75/04* (2013.01)

(56) References Cited

U.S. PATENT DOCUMENTS

| | | | |
|---|---|---|---|
| 6,518,374 B1* | 2/2003 | Aichinger | C08F 2/42 252/394 |
| 6,579,442 B2* | 6/2003 | Eldin | C07B 63/04 203/8 |
| 8,691,994 B2* | 4/2014 | Tong | C07C 7/20 526/335 |
| 9,399,622 B2 | 7/2016 | Tong | |
| 9,725,649 B2 | 8/2017 | Subramaniyam | |
| 2003/0049161 A1* | 3/2003 | Blaschke | C07B 63/04 422/16 |
| 2005/0183942 A1* | 8/2005 | Blaschke | C07B 63/04 203/6 |
| 2005/0261440 A1* | 11/2005 | Dickakian | C08F 8/32 525/333.7 |
| 2012/0203020 A1 | 8/2012 | Tong | |
| 2013/0288937 A1* | 10/2013 | Cooney | C10L 1/221 508/449 |
| 2015/0218468 A1* | 8/2015 | Ovaskainen | C10G 75/04 422/7 |

FOREIGN PATENT DOCUMENTS

| | | |
|---|---|---|
| EP | 1897908 A1 | 3/2008 |
| KR | 101625041 B1 | 5/2016 |
| WO | 20100094982 A1 | 8/2010 |

OTHER PUBLICATIONS

Written Opinion for International Application No. PCT/US2018/019448, dated May 14, 2018, 7 pages.

* cited by examiner

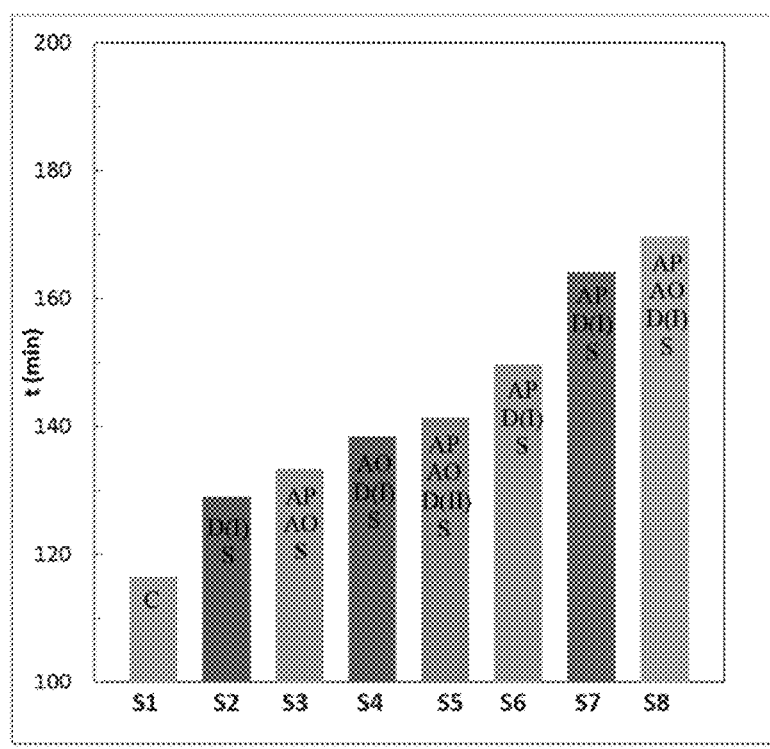

ANTI-FOULANT FORMULATION FOR COMPRESSORS

CROSS REFERENCE TO RELATED APPLICATIONS

This application claims the benefit of U.S. Provisional Patent Application Ser. No. 62/463,790, filed Feb. 27, 2017, the disclosure of which is incorporated in its entirety herein by reference.

TECHNICAL FIELD

The invention is directed at an antifoulant composition and its use with compressors.

BACKGROUND

Fouling of compressors is a well-known problem in processes using them such as cracked gas compression systems in ethylene processes. Steam cracking of hydrocarbons accounts for virtually all of the ethylene produced worldwide. In the process of producing ethylene, small polymer amounts can form. These polymers are generally considered contaminants and are undesirable.

The polymer contaminants cause issues in cracked gas compression systems, which are multi-stage systems that include multiple gas compressors and inter-coolers. The polymers foul machines by depositing on, for example, the internal surfaces of compressors and inter-coolers resulting in reduced efficiency of the process and in some cases blocking the flow path and stopping production and in severe cases, damaging parts.

Premature polymerization of ethylenically unsaturated monomers is a major polymer formation mechanism in monomer manufacturing process such as antifoulant processes. Ethylenically unsaturated monomers in these process streams are reactive and tend to polymerize through radical polymerization and Diels-Alder polymerization to form solid deposits, especially at elevated temperatures.

The frequent fouling and the need to clean can be a burden to production and efficiency of the operations.

SUMMARY

Disclosed are compositions and methods for reducing fouling thereby improving energy efficiency of a system and preventing product quality issues.

In one aspect of the invention is disclosed an antifoulant composition comprising a combination of one or more antioxidants; one or more antipolymerants; one or more dispersants; and one or more solvents.

In yet another aspect of the invention is disclosed a method of preventing or reducing fouling of process equipment used in an industrial process comprising:

introducing into the process equipment an antifoulant composition, the antifoulant composition comprising a combination of:
one or more antioxidants;
one or more antipolymerants;
one or more dispersants; and
one or more solvents.

The disclosed composition has use in reducing or preventing fouling of process equipment in an antifoulant process.

BRIEF DESCRIPTION OF THE DRAWINGS

FIG. 1 is a graphical representation of the effect of various antifoulant compositions of the invention on the gelation time of a simulated pygas mixture.

DETAILED DESCRIPTION

Although the present disclosure provides references to embodiments, persons skilled in the art will recognize that changes may be made in form and detail without departing from the spirit and scope of the invention. Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

Definitions

As used herein, the term "antifoulant" refers to a composition that reduces or prevents the deposition of material such as polymers, prepolymers, oligomers and/or other materials on "process equipment." The term can also refer to a composition that reduces or prevents the formation of radically polymerizable species.

As used herein, the term "antioxidant" refers to compound(s) capable of scavenging oxygen-centered radicals through donating a hydrogen radical (H) to the oxygen-centered radicals.

As used herein, the term "antipolymerants" refers to stable free radicals that are efficient in capturing or scavenging carbon-centered radicals through coupling reactions.

Antioxidants and antipolymerants are sometimes referred to as polymerization "chain stoppers."

As used herein, the term "process equipment" means compressors, fans, impellers, pumps, valves, inter-coolers, sensors, and the like, that are associated with the process and which may be subject to fouling. This term also includes sets of components which are in communication such as, for example, a gas compressor in an antifoulant process.

As used herein, the term "process condensate" means water plus one or more pyrolysis byproducts present within a petrochemical processing system. In some embodiments, the process condensate includes pygas, pygas byproducts, or a mixture thereof.

As used herein, the term "pygas" is a term of art and shorthand for "pyrolysis gasoline." Pygas is a pyrolysis byproduct that is less dense than water and is a mixture of petroleum based products that condenses along with water in the quench water tower of a dilution steam system of an industrial processing plant, such as a pyrolysis plant. Pygas is a variable mixture of hydrocarbons and other byproducts, wherein the mixture components and amounts are determined by the feedstock and conditions employed in the pyrolysis. As determined by context and/or unless otherwise specified, pygas includes one or more aromatic compounds and a mixture of alkanes and alkenes having at least 5 carbons, wherein a majority (i.e., more than 50 wt %) of the alkane/alkene component is $C_5$-$C_{12}$. In some embodiments, pygas is rich in benzene (for example, 20 wt %-45 wt %). Pygas also contains highly reactive olefins and diolefins such as styrene, isoprene, piperylenes, cyclopentadienes, and combinations thereof. In some embodiments, pygas further includes components such as $C_1$-$C_5$ organic acids. In some embodiments, pygas includes about 0.01 wt % to as much as about 20 wt % pytar based on the total weight of a pygas-pytar mixture, where the amount of pytar depends on the individual equipment employed for cracking and the feedstock. Unless otherwise specified, or in context, "pygas" includes both pygas and mixtures thereof with pytar, pygas byproduct, or both.

As used herein, the term "pytar" is a term of art and shorthand for "pyrolysis tar". Pytar is a pyrolysis byproduct that is denser than water and is a mixture of petroleum based products that condenses along with water in the quench water tower of a dilution steam system of a pyrolysis plant. The term indicates a mixture of >$C_{12}$ alkanes/alkenes and/or ≥C10 polyaromatic hydrocarbons including, for example, anthracene, phenanthrene, pyrene, chrysene, fluoranthene, and others as well as mixtures of two or more thereof and with similar compounds along with variants that have a random distribution of substituents such as methyl, ethyl, and higher alkyl or alkenyl substituents As used herein, the term "pygas byproduct" means any one or more compounds formed as the product of a chemical reaction of one or more components of pygas (including pygas-pytar mixtures) wherein the reaction takes place within a dilution steam system of a pyrolysis plant, further wherein the reaction results in an increase in molecular weight of one or more of the reacted components. In some embodiments, a pygas byproduct includes an oligomerized or polymerized residue of styrene and/or one or more unsaturated and radically polymerizable components of the pygas.

As used herein, the chemical names of polymerizable species (such as, e.g. acrylic acid, styrene, and the like) are used to mean either the chemical species itself or the polymerized residue thereof in one or more polymers, as determined by context.

As used herein, the term "optional" or "optionally" means that the subsequently described event or circumstance may but need not occur, and that the description includes instances where the event or circumstance occurs and instances in which it does not.

As used herein, the term "about" modifying, for example, the quantity of an ingredient in a composition, concentration, volume, process temperature, process time, yield, flow rate, pressure, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities. Further, where "about" is employed to describe any range of values, for example "about 1 to 5" the recitation means "1 to 5" and "about 1 to about 5" and "1 to about 5" and "about 1 to 5" unless specifically limited by context.

As used herein, the word "substantially" modifying, for example, the type or quantity of an ingredient in a composition, a property, a measurable quantity, a method, a position, a value, or a range, employed in describing the embodiments of the disclosure, refers to a variation that does not affect the overall recited composition, property, quantity, method, position, value, or range thereof in a manner that negates an intended composition, property, quantity, method, position, value, or range. Examples of intended properties include, solely by way of nonlimiting examples thereof, flexibility, partition coefficient, rate, solubility, temperature, and the like; intended values include thickness, yield, weight, concentration, and the like. The effect on methods that are modified by "substantially" include the effects caused by variations in type or amount of materials used in a process, variability in machine settings, the effects of ambient conditions on a process, and the like wherein the manner or degree of the effect does not negate one or more intended properties or results; and like proximate considerations. Where modified by the term "substantially" the claims appended hereto include equivalents to these types and amounts of materials.

As used herein, any recited ranges of values contemplate all values within the range and are to be construed as support for claims reciting any sub-ranges having endpoints which are real number values within the recited range. By way of a hypothetical illustrative example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5.

Discussion

Disclosed herein are antifoulant compositions and methods of preventing or reducing fouling in systems used in for example hydrocarbon cracking. The antifoulant composition contains a combination of components such as one or more antioxidants, one or more antipolymerants, one or more dispersants and one or more solvents. While components such as antioxidants and antipolymerants have been shown separately or in combination to be effective at preventing polymerization and fouling, the antifoulant composition is shown herein to have a greater than additive effect. In other words, the combination of components performs better together than the each individual component separately.

Antioxidants

The antifoulant compositions include one or more antioxidants that can work against, for example, ethylenically unsaturated monomers. The antioxidant is a compound or blend thereof.

Exemplary antioxidants include phenolic antioxidants, such as phenylenediamines and hindered phenols thereof that are known to prevent unwanted polymerization of ethylenically unsaturated monomers.

In some embodiments, the phenolic antioxidant can include hindered and nonhindered phenols targeted toward an ethylenically unsaturated monomer. Examples of such phenolic antioxidants are hydroquinone (HQ), butylated hydroxytoluene (BHT), TBC, 2,6 di-tert-butyl phenol and monomethylether of hydroquinone (MEHQ).

In some embodiments the phenylenediamines can include an unsubstituted phenylenediamine, N-substituted phenylenediamine or N,N'-substituted phenylenediamine targeted towards an ethylenically unsaturated monomer, and any combination thereof. Examples of phenylenediamine are 1,4-phenylenediamine, N,N'-dimethyl-p-phenylenediamine, N,N'-di-sec-butyl-p-phenylenediamine, N-phenyl-N'-dibutyl-p-phenylenediamine, N-phenyl-N'-(1,4-dimethylphenyl)-p-phenylenediamine, N-phenyl-N'-(1,3-dimethylbutyl)-p-phenylenediamine, and any combination thereof.

Phenylenediamines can also include p- or m-phenylenediamine itself (PDA); N,N'-dipllenylphenylenediamine;

N,N,N',N'-tetramethyl-p-phenylenediamine; N,N'-bis-(1,4-dimethylpentyl)--phenylenediamine; N-phenyl-N'-(1,4-dimethylpentyl) p-phenylenediamine; N-phenyl-N'-(1,3-dimethylbutyl) p-phenylenediamine; N-phenyl-N-cyclohexyl p-phenylenediamine; N,N'-dinaphthyl p-phenylenediamine; N-isopropyl-N'-phenyl p-phenylenediamine; N-aminoalkyl-N'-phenyl p-phenylenediamine; N-(2-methyl-2-aminopropyl)-N'-phenyl p-phenylenediamine; phenyl-b-isopropyl-aminophenylamine; p-hydroxydiphenylamine; p-hydroxylphenyl-b-naphthylamine; 1,8-naphthalenediamine.

Hindered phenolic compounds can include o- and p-sec-butylphenol; 2,4-di-sec-butylphenol; 2,6-di-sec-butylphenol; 2,4,6-tri-sec-butylphenol; 2,4,6-trimethylphenol; butylated hydroxytoluene (BHT, also known as 2,6-tert-butyl-4-methylphenol and 2,6-tert-butyl p-cresol); 2,6-dibutyl-4-methylphenol; hydroquinone; monomethylether of hydroquinone (MEHQ); 2,6-bis (1,6 dimethylethyl-4-(1-methylpropyl) phenol), b-naphthoquinone; N-phenyl p-aminophenol; and combinations thereof.

In some embodiments, the antioxidant is selected from 1,4-phenylenediamine, alkylated or phenyl derivatives thereof, and combinations thereof. Exemplary alkylated or phenyl derivatives include N,N'-Di-2-butyl-1,4-phenylenediamine and N-2-butyl-N'-phenyl-1,4-phenylenediamine.

In some embodiments, the antioxidant or blend thereof is present at about 0.5 wt % to about 50 wt %, or about 1 wt % to about 50 wt %, about 1 wt % to about 30 wt %, about 1 wt % to about 20 wt %, 1 wt % to 10 wt %, 2 wt % to about 30 wt %, about 2 wt % to about 20 wt % or about 2 wt % to 10 wt % of the antifoulant composition.

Antipolymerants

The antifoulant compositions also include antipolymerants. Suitable antipolymerants include the following groups of chemicals: nitroxides (e.g., di-tert-butylnitroxide), hindered phenoxy compounds (e.g., galvinoxyl), hydrazyl compounds (e.g., diphenylpicrylhydrazyl), and stabilized hydrocarbon radicals (e.g., triphenylmethyl), as well as polyradicals, preferably biradicals of these types. In addition, certain precursors that produce stable free radicals in situ may be selected from the following groups: nitrones, nitrosos, thioketones, benzoquinones, and hydroxylamines.

Exemplary antipolymerants include one or more of 2,2,6,6-tetramethylpiperidinyl-1-oxyl (TEMPO), 1-hydroxy-2,2,6,6-tetramethylpiperidine (TEMPOH), 4-hydroxy-2,2,6,6-tetramethylpiperidinyl-1-oxyl (HTMPO), 4-oxo-2,2,6,6-tetramethylpiperidinyl-1-oxyl (OTEMPO), 1,4-dihydroxy-2,2,6,6-tetramethylpiperidine (HTMPOH), and 1-hydroxy-4-oxo-2,2,6,6-tetramethylpiperidine (OTEMPOH) or a combination thereof.

Other exemplary antipolymerants include 4-methoxy-2,2,6,6-tetramethylpiperidine-1-oxide, 4-ethoxy-2,2,6,6-tetramethylpiperidine-1-oxide, 4-propoxy-2,2,6,6-tetramethylpiperidine-1-oxide, 4-butoxy-2,2,6,6-tetramethylpiperidine-1-oxide, 4 4-acetate-2,2,6,6-tetramethyl piperidinol, 4-amino-2,2,6,6-tetramethyl piperidinol, 4-acetamido-2,2,6,6-tetramethyl piperidinol, 1,2,3,6-tetrahydro-2,2,6,6-tetramethyl piperidinol, bis(2,2,6,6-tetramethylpiperidinol) sebacate, add 3,6-dihydro-2,2,6,6-tetramethyl-1(2H)pyridinyloxy or a combination thereof.

In some embodiments, the antipolymerant is 4-hydroxy-2,2,6,6-tetramethylpiperidyl-1-oxyl.

Other suitable agents to use as an antipolymerant are disclosed in U.S. Pat. No. 9,399,622, which is incorporated herein by reference in its entirety and for all purposes.

In some embodiments, the antipolymerants are present at about 0.5 wt % to about 30 wt %, or about 1 wt % to about 30 wt %, 1 wt % to about 25 wt %, about 1 wt % to about 20 wt %, 1 wt % to about 10 wt %, 2 wt % to about 30 wt %, about 2 wt % to about 25 wt %, about 2 wt % to about 20 wt %, or 2 wt % to about 10 wt %, of the antifoulant composition.

Dispersants

The antifoulant compositions include one or more dispersants. The dispersant may impart one or more advantageous properties to the antifoulant composition, for example, increased separation of unsaturated species, leading to decreased degree of polymerization thereof; and/or increased flotation of reacted species, leading to reduced polymer deposition on equipment such as on the compressor inner surfaces.

Suitable dispersants present in the antifoulant composition include amides of fatty acids. Suitable fatty acids employed to form the dispersants include unsaturated fatty acids, that is, mono- or polyunsaturated long-chain acids derived from sources comprising, consisting essentially of, or consisting of tall oil (tall oil fatty acids, or TOFA), coconut oil, canola oil, palm seed oil, and the like. TOFA can be obtained by fractional distillation and other purification processes carried out on tall oil. Tall oil, or tallol, is obtained as a by-product of the Kraft process of wood pulp manufacture, principally from pulping coniferous trees. Crude tall oil contains rosins, fatty acids and fatty alcohols, sterols, and other alkyl hydrocarbon derivatives. The majority component of TOFA after purification of crude tall oil typically includes oleic acid.

The diamines comprise, consist essentially of, or consist of diamines. The diamines can include compounds having at least two amine groups and include polyamines. The diamines can be primary, secondary or tertiary. Exemplary diamines include triethanolamine (TEA), diethylenetriamine (DETA), triethylenetetraamine (TETA), tetraethylenepentamine (TEPA), and other such compounds.

The dispersant can include blends of two or more fatty acid amides. The two or more fatty acid amides can be different. In some embodiments, the dispersant can include a blend of two or more fatty acid amides in the mass ratio of about 10:1 to 1:10, or from about 1:1 to 1:10 or from about 1:1 to 1:2.

In some embodiments, the dispersant is a reaction product of a tall oil fatty acid and a trimethylamine. The resultant fatty acid amide product is referred herein as P1. The dispersant can also be formed from a tall oil fatty acid and a tetraethylpentamine, in which the resultant fatty acid amide product is referred herein as P2. In some embodiments, the dispersant can include fatty acid amides products P1:P2 in the ratio of about 10:1 to 1:10, or from about 1:1 to 1:10 or from about 1:1 to 1:2.

In some embodiments, the dispersant is present at about 50 wt % to about 90 wt % of the weight of the antifoulant composition, or 60 wt % to 90 wt %, 70 wt % to about 90 wt % or 60 wt % to 70 wt % of the antifoulant composition.

Solvent

The antifoulant compositions also include one or more solvents. Suitable solvents include any solvent in which a combination of the antipolymerants, antioxidants and dispersants are soluble or dispersible. In some embodiments, the solvents are water soluble or miscible solvents such glycol-based. In some embodiments the solvents are hydrophobic solvents such as aromatic solvents, paraffinic solvents. In some embodiments, the solvents can be mixtures of glycol-based solvents and hydrophobic solvents.

Exemplary glycol solvents include, but are not limited, $C_1$-$C_8$ glycols such as ethylene glycol, propylene glycol, diethylene glycol, and triethylene glycol, ethers of such glycols such as diethylene glycol monobutyl ether, diethylene glycol monomethyl ether, diethylene glycol monoethyl ether, diethylene glycol monobutyl ether, triethylene glycol, triethylene glycol monomethyl ether, liquid polyethylene glycol, dipropylene glycol, dipropylene glycol monomethyl ether, dipropylene glycol monoethyl ether, and a low molecular weight polypropylene glycol and the like and combinations thereof. Commercial solvents such as Butyl Carbitol and Butyl CELLOSOLVE™, may be used and are available from Dow Chemical Company of Midland, Mich.

Exemplary hydrophobic solvents include heavy aromatic naphtha, toluene, ethylbenzene, and isomeric hexanes, and mixtures of two or more thereof.

In some embodiments, the solvent is selected from glycol, aromatic naphtha or glycol and aromatic naptha.

The concentration of one or more solvents in the antifoulant composition is not particularly limited. In some embodiments, the concentration of one or more solvents can be about 10 wt % to 50 wt %, about 20 wt % to 50 wt %, or about 30 wt % to 50 wt %, or about 10 wt % to 40 wt %, or about 10 wt % to 30 wt %, or about 20 wt % to 40 wt %, or about 30 wt % to 40 wt % of the antifoulant composition.

In some embodiments, the antifoulant composition includes from about 1 wt % to about 15 wt % antioxidant; about 1 wt % to about 15 wt % antipolymerant; about 50 wt % to about 95 wt % dispersant and from about 10 wt % to about 50 wt % solvent in the antifoulant composition.

In some embodiments, the antifoulant composition includes from about 1 wt % to about 15 wt % 1,4-phenylenediamine, alkylated or phenyl derivatives; 1 wt % to about 15 wt % 4-hydroxy-2,2,6,6-tetramethylpiperidinyl-1-oxyl; about 50 wt % to about 95 wt % of a product of tall oil and a diamine and from about 10 wt % to about 50 wt % glycol and aromatic naphtha.

While the amount of antifoulant composition used depends on a number of factors, exemplary amounts introduced into process equipment and process condensate (through either injection into the feed stream or direct injection to each compression stage) range from about 1 ppm to 500 ppm of the combination of the antifoulant composition, or about 5 ppm to 500 ppm, 10 ppm to 500 ppm, or about 20 ppm to 500 ppm, or about 30 ppm to 500 ppm, or about 40 ppm to 500 ppm, or about 50 ppm to 500 ppm, or about 60 ppm to 500 ppm, or about 70 ppm to 500 ppm, or about 80 ppm to 500 ppm, or about 90 ppm to 500 ppm, or about 100 ppm to 500 ppm, or about 5 ppm to 450 ppm, or about 5 ppm to 400 ppm, or about 5 ppm to 350 ppm, or about 5 ppm to 300 ppm, or about 5 ppm to 250 ppm, or about 5 ppm to 200 ppm, or about 5 ppm to 150 ppm, or about 5 ppm to 100 ppm, or about 10 ppm to 300 ppm, or about 10 ppm to 250 ppm, or about 50 ppm to 250 ppm, or about 50 ppm to 200 ppm based on the antifoulant compositions.

Processes and Applications

The antifoulant compositions are useful in preventing or reducing deposition of polymers and in some cases reducing or preventing polymer formation in process equipment such as gas compressors used in ethylene production processes. The antifoulant composition can also be useful in other similar applications and with other equipment. For example, the antifoulant composition may be used with any process where process equipment will come into contact with ethylenically unsaturated monomers, such as in an ethylene cracked gas process. Another application is ethylene and acrylonitrile quench water systems. The antifoulant composition may be used with ethylene dilution steam generators and acrylonitrile purification systems. Many polymer processes have monomer recovery systems which are subject to fouling and are good target applications for the antifoulant composition. Process water strippers and waste water strippers used with petrochemical processes such as styrene, butadiene, acrylonitrile, and ethylene processes are potential applications for the antifoulant composition. In some embodiments, ethylene acid gas scrubbers and butadiene solvent recovery systems are also end use applications of antifoulant composition. The antifoulant composition can be used in any process which has process equipment subject to polymers forming and depositing on process equipment. In addition to processes that consume or produce at least one of styrene, butadiene, acrylonitrile, and ethylene are potential applications of the antifoulant composition.

In embodiments, the antifoulant composition can prevent polymerization and deposition of the polymers on process equipment in a primary fractionation process, light ends fractionation, non-aromatic halogenated vinyl fractionation, process-gas compression, dilution steam system, caustic tower, quench water tower, butadiene extraction. In some embodiments, the antifoulant composition can prevent or reduce or delay the polymerization of resins and compositions comprising ethylenically unsaturated species.

The antifoulant composition may be added at one or more points in a process and at one or more locations. For example, the antifouling composition can be added directly at an inter-coolers or compressors or upstream of the inter-coolers or different stages of the same compressor.

The antifoulant composition can be added continuously or intermittently to the process equipment as required to prevent or to reduce fouling.

The antifoulant composition may be added by any suitable method. For example the antifoulant composition may be added in neat or a dilute solution. In some embodiments, the antifoulant composition may be applied as a solution, emulsion, or dispersion that is sprayed, dripped, poured or injected into a desired opening within a system or onto the process equipment or process condensate. In some embodiments, the antifoulant composition may be added with a washoil or an attemperation water.

In some embodiments, the antifoulant composition can be pumped or injected into a system in a continuous fashion or as a high volume flush to clean the system. The injection point can be at any or all stages of the compressor train and/or to the discharge lines before each after cooler.

The antifoulant composition is applied to a process equipment to form a treated process equipment. In some embodiments, treated process equipment can be observed to undergo less polymer deposition on process equipment than on process equipment without addition of the antifoulant composition. Reduction or prevention in the polymer formation or polymer deposition can be evaluated by any known method or test. In some embodiments, the reduction or prevention of polymer formation and polymer deposition on process equipment can be assessed by measuring the time it takes for the process equipment with and without the antifoulant composition to gel. The longer a process equipment takes to form and/or deposit a gel the more effective the antifoulant composition is at reducing formation of polymers and deposition of polymers on process equipment.

The effect of the antifoulant composition can also be evaluated by measuring the time it takes for a simulated pygas mixture gel. Simulated pygas removes any variability of pygas compositions from plant to plant. A simulated pygas mixture can contain, for example, conjugated diene (isoprene), vinyl monomer (ethenylbenzene), dimer of cyclopentadiene, and crosslinker (divinylbenzene). In some embodiments, the simulated pygas mixture contains 25 wt/vol % conjugated diene (isoprene), 48 wt/vol % vinyl monomer (ethenylbenzene), 25 wt/vol % dimer of cyclopentadiene, and 2 wt/vol % crosslinker (divinylbenzene). In some embodiments, using the measurements described above, polymer formation and solid deposition inside process equipment treated with the antifoulant composition is reduced by at least 50 wt % compared to process equipment not treated with the antifoulant composition. In some embodiments, about 50 wt % to 100 wt % (where 100 wt % reduction in polymer formation is elimination of deposition), or about 50 wt % to 95 wt %, or about 50 wt % to 90 wt %, or about 50 wt % to 85 wt %, or about 50 wt % to 80 wt %, or about 50 wt % to 75 wt %, or about 50 wt % to 70 wt %, or about 55 wt % to 100 wt %, or about 60 wt % to 100 wt %, or about 65 wt % to 100 wt %, or about 70 wt % to 100 wt %, or about 60 wt % to 95 wt %, or about 70 wt % to 95 wt %, or about 60 wt % to 90 wt %, or about 70 wt % to 90 wt %.

In some embodiments, fouling of treated process equipment is reduced by 50 wt % to 100 wt % compared to untreated process equipment over a 24 hour period, or 12 hour period or 1 hour period. The longer the time period of gel formation in a process equipment treated with the antifoulant composition, the less or delayed the deposition of polymers on process equipment.

EXAMPLES

The following examples are intended to illustrate different aspect and embodiment of the invention and are not to be considered limiting the scope of the invention. It will be recognized that various modifications and changes may be made without following the experimental embodiments described herein, further without departing from the scope of the claims.

Example 1

Materials Used: A simulated pygas mixture contained 25 wt/vol % conjugated diene (isoprene), 48 wt/vol % vinyl monomer (ethenylbenzene), 25 wt/vol % dimer of cyclopentadiene, and 2 wt/vol % crosslinker (divinylbenzene).

A solvent free N,N'-Di-Sec-Butyl-1,4-Phenylenediamine (PDA) and a stock solution of known concentration of 4-Hydroxy-2,2,6,6-tetramethylpiperidyl-1-oxyl (HTMPO) in aromatic naphtha was further diluted with glycol based co-solvent.

Aromatic naphtha (C10+) and butyl glycol was used as co-solvent. Solvent and co-solvent were used in equal weight percentage amounts.

Three dispersants, Dispersant type I, type II and type III were used and prepared as follows:

Dispersant type I is a blend of two fatty acid amides. A tall oil fatty acid (TOFA) and trimethylamine (TEA) were combined to result in product 1 (P1). A TOFA was combined with tetraethylenepentamine (TEPA), which was diluted in xylene to result in product 2 (P2) or abbreviated as shown below:

TOFA+TEA: P1
or
TOFA+TEPA: P2

Ratios of P1:P2 in dispersant type I was 3.6:1.

Dispersant type II was prepared similarly to Dispersant type 1 except the ratio of P1:P2 was 7.8:1.

Dispersant type III was a methacrylated copolymer (methacrylate C4 to C18 polymer) in paraffinic oil available as Texaco TC-8103 from Afton Chemicals.

A stock solution of known concentration of HTMPO in aromatic naphtha was further diluted with glycol based co-solvent. PDA was added to the mixture along with dispersant type I, II or III. The mixture was vigorously mixed until all solid was dissolved and the solution was homogeneous.

Five hundred ppm of each formulation as shown in Table 1 was dosed into the simulated pygas mixture in sealed pressure rated tubes and vigorously mixed. Each tube was then purged with 100% nitrogen for 1 minute and tightly capped. The tubes were placed in a temperature controlled environment with temperature set to 130° C. The gelation point, the onset of solidification of the mixture, was determined by turning the tubes upside down and monitoring the flow. Each formulation was tested in triplicate and the data reported is an average of the three test results for each sample. The data is reported as the time it took for the simulated pygas mixture to gel. After the first tube gelled, the other samples were checked every five minutes.

The formulations of the antifoulant composition with weight percentage dosed into the pygas mixture are shown in Table 1. The results of the time it takes to gel for each formulation is shown in Table 1 and FIG. 1.

TABLE 1

Formulations Dosed to a Simulated Pygas Mixture

| | $S_1$ Control | $S_2$ | $S_3$ | $S_4$ | $S_5$ | $S_6$ | $S_7$ | $S_8$ |
|---|---|---|---|---|---|---|---|---|
| PDA (wt %) | — | — | 2.5 | 2.5 | 2.5 | — | — | 2.5 |
| HTMPO wt % | — | — | 2.5 | — | 2.5 | 2.5 | 2.5 | 2.5 |
| Dispersant type I (wt %) | — | 74 | — | 74 | — | — | 74 | 74 |
| Dispersant type II (wt %) | — | — | — | — | — | 79 | — | — |
| Dispersant type III (wt %) | — | — | — | — | 74 | — | — | — |
| Solvent (wt %) | — | 26 | 95 | 23.5 | 21 | 18.5 | 23.5 | 21 |
| Total (wt %) | 0 | 100 | 100 | 100 | 100 | 100 | 100 | 100 |
| Time to gel (min) | 116 | 129 | 133 | 138 | 141 | 150 | 164 | 170 |

As shown in Table 1, the control experiment $S_1$ showed the shortest time to gel, whereas $S_8$ showed the longest time to gel. The addition of dispersant, PDA and HTMPO increased the time to gel as shown by $S_2$, $S_3$, and $S_4$. The difference between $S_5$ and $S_8$ was related to the dispersant type (type III vs. type I). The difference between $S_6$ and $S_7$ samples lies in the ratio of dispersant type (I) vs. type (II). When the dispersant components are used as type (I), the gelation time increased from 150 to 165 min (10%). The difference between $S_7$ and $S_8$ demonstrates the cumulative effects of antipolymerant, antioxidant, and dispersant. S8 showed the longest time to gel. This time was greater than an additive effect as measured by time to gel.

The invention illustratively disclosed herein can be suitably practiced in the absence of any element which is not specifically disclosed herein. Additionally each and every embodiment of the invention, as described herein, is intended to be used either alone or in combination with any other embodiment described herein as well as modifications, equivalents, and alternatives thereof. In various embodiments, the invention suitably comprises, consists essentially of, or consists of the elements described herein and claimed according to the claims. It will be recognized that various modifications and changes may be made without following the example embodiments and applications illustrated and described herein, and without departing from the scope of the claims.

What is claimed is:

1. An antifoulant composition comprising:
   a combination of one or more antioxidants selected from 1,4-phenylenediamine, alkylated or phenyl derivatives thereof, and combinations thereof;
   one or more antipolymerants selected from 2,2,6,6-tetramethylpiperidinyl-1-oxyl, 1-hydroxy-2,2,6,6-tetramethylpiperidine, 4-hydroxy-2,2,6,6-tetramethylpiperidinyl-1-oxyl, 4-oxo-2,2,6,6-tetramethylpiperidinyl-1-oxyl, 1,4-dihydroxy-2,2,6,6-tetramethylpiperidine, and 1-hydroxy-4-oxo-2,2,6,6-tetramethylpiperidine, or a combinations thereof;
   one or more dispersants, wherein the dispersant is a blend of two or more fatty acid amides, wherein a first fatty acid amide is a tetraethylenepentamine of tall oil and a second fatty acid amide is a triethanolamine of tall oil; and
   one or more solvents.

2. The composition of claim 1, wherein the antifoulant composition comprises from about 1 wt % to about 15 wt % antioxidant; about 1 wt % to about 15 wt % antipolymerant; about 50 wt % to about 95 wt % dispersant and about 10 wt % to about 50 wt % solvent.

3. The composition of claim 1, wherein the blend is a ratio of the first fatty acid amide to the second fatty acid amide is about 1:1 to about to 1:10 or from about 1:1 to about 1:2.

4. The composition of claim 1, wherein the solvent is selected from glycol and aromatic naphtha and combinations thereof.

* * * * *